(12) United States Patent
Heo et al.

(10) Patent No.: US 9,642,697 B2
(45) Date of Patent: May 9, 2017

(54) BREAST PROSTHESIS ALLOWING CONTROLLED RELEASE OF DRUG AND PRODUCTION METHOD FOR SAME

(71) Applicant: SNU R&DB FOUNDATION, Seoul (KR)

(72) Inventors: Chan Yeong Heo, Yongin-si (KR); Young Bin Choy, Seongnam-si (KR); Min Park, Seoul (KR); Su Bin Park, Seoul (KR); Won Seok Lee, Seoul (KR); Byung Hwi Kim, Yongin-si (KR)

(73) Assignee: SNU R&DB FOUNDATION, Seoul (KR)

( * ) Notice: Subject to any disclaimer, the term of this patent is extended or adjusted under 35 U.S.C. 154(b) by 130 days.

(21) Appl. No.: 14/396,982

(22) PCT Filed: Apr. 24, 2013

(86) PCT No.: PCT/KR2013/003486
§ 371 (c)(1),
(2) Date: Apr. 20, 2015

(87) PCT Pub. No.: WO2013/162270
PCT Pub. Date: Oct. 31, 2013

(65) Prior Publication Data
US 2015/0313707 A1    Nov. 5, 2015

(30) Foreign Application Priority Data

Apr. 24, 2012    (KR) ........................ 10-2012-0042895

(51) Int. Cl.
*A61F 2/12*    (2006.01)
*A61L 27/54*    (2006.01)

(52) U.S. Cl.
CPC ................ *A61F 2/12* (2013.01); *A61L 27/54* (2013.01); *A61F 2210/0061* (2013.01); *A61F 2210/0076* (2013.01); *A61F 2240/001* (2013.01); *A61F 2240/002* (2013.01); *A61F 2250/0067* (2013.01); *A61F 2250/0068* (2013.01); *A61F 2310/0097* (2013.01); *A61L 2300/602* (2013.01); *A61L 2430/04* (2013.01)

(58) Field of Classification Search
CPC ........................................................ A61F 2/12
USPC ........................................................ 623/7–8
See application file for complete search history.

(56) References Cited

U.S. PATENT DOCUMENTS 5,376,117 A * 12/1994 Pinchuk ................ A61F 2/0077
                                                                        623/8
8,420,153 B2 * 4/2013 Berg ........................ A61L 27/34
                                                                        427/2.24
(Continued)

FOREIGN PATENT DOCUMENTS

JP    2011-528275 A    11/2011
KR    10-0358080 B1    10/2002
(Continued)

*Primary Examiner* — Suzette J Gherbi
(74) *Attorney, Agent, or Firm* — Seed IP Law Group LLP

(57) ABSTRACT

The present invention relates to a breast prosthesis allowing controlled release of a drug and to a production method for same, and more specifically, relates to a breast prosthesis allowing controlled release of a drug by the coupling of a drug layer comprising particles carrying the drug on the breast prosthesis, and to a production method for same.

16 Claims, 12 Drawing Sheets

(56) References Cited

U.S. PATENT DOCUMENTS

| | | | |
|---|---|---|---|
| 2008/0241212 A1* | 10/2008 | Moses | A61F 2/12 424/423 |
| 2010/0168808 A1* | 7/2010 | Citron | A61L 31/10 607/5 |
| 2011/0082545 A1* | 4/2011 | Freund | A61F 2/12 623/8 |
| 2011/0082546 A1* | 4/2011 | Freund | A61F 2/12 623/8 |
| 2012/0121661 A1* | 5/2012 | Schwartz | A61L 27/32 424/400 |
| 2013/0110237 A1* | 5/2013 | Schaer | A61F 2/02 623/11.11 |

FOREIGN PATENT DOCUMENTS

| | | |
|---|---|---|
| KR | 10-0496353 B1 | 6/2005 |
| KR | 10-2005-0088288 A | 9/2005 |
| KR | 10-2008-0034089 A | 4/2008 |
| KR | 10-2008-0073328 A | 8/2008 |
| KR | 10-2010-0130078 A | 12/2010 |
| KR | 10-1067475 B1 | 9/2011 |

\* cited by examiner

BREAST PROSTHESIS ALLOWING CONTROLLED RELEASE OF DRUG AND PRODUCTION METHOD FOR SAME

TECHNICAL FIELD

The present invention relates, in general, to a breast prosthesis allowing controlled release of drugs and a method of manufacturing the same. More particularly, the present invention relates to a breast prosthesis allowing controlled release of drugs in vivo after implantation and a method of manufacturing the same.

BACKGROUND ART

Recently, the breast prosthesis market has been growing quickly owing to the rapid increase in breast reconstruction due to breast-related diseases such as breast cancer and to mastoplasty conducted for beauty purposes.

A breast prosthesis implantation generally accompanies a foreign body reaction which allows fibrous tissues to surround the implanted breast prosthesis, thereby causing a capsular contracture. Accordingly, patients with a breast prosthesis implant suffer from inflammation, along with pains, thus necessitating administration of drugs for at least two weeks and up to a year. Further, the long-term administration of drugs often causes the patients to suffer a financial burden and have adverse drug reactions due to the frequent administration and large amount of drugs.

Considering the growing market of breast prosthesis implantation, a controlled, local delivery of drug with drug-loaded particles directly mounted on a breast prosthesis, capable of resolving the above-mentioned problems such as fibrosis, would enable the development of value-added breast prosthesis.

In the conventional breast prosthesis loaded with drugs to prevent capsular contracture, it is difficult to acquire a reproducible amount of a drug due to lack of quantitative analysis loaded onto the breast prosthesis.

Additionally, due to a lack of sufficient systemic analysis of the in vitro and in vivo release behaviors of the drugs loaded in breast prosthesis, it is not possible to determine the optimal therapeutic effects based on the duration of drug delivery and the drug dose.

Accordingly, there is a need for the development of breast prosthesis capable of providing controllable and programmable access to drug delivery images.

Additionally, considering that most of the currently available drugs in the art are orally administered for at least two weeks to up to a year, long-duration sustained drug release is required for local delivery.

As such, the present inventors, while endeavoring to solve the above problems, discovered that breast prosthesis capable of controlled release of a drug can be provided by binding a drug layer containing drug-loaded nano-, micro-, centi- or millimeter-sized particles onto a breast prosthesis, thereby completing the present invention.

DISCLOSURE

Technical Problem

Accordingly, the present invention has been made keeping in mind the above problems occurring in the prior art, and an objective of the present invention is to provide a breast prosthesis capable of a controlled release of a drug.

Another objective of the present invention is to provide a method for manufacturing a breast prosthesis independently capable of a controlled release of more than one kind of drug.

Technical Solution

In order to accomplish the above objectives, the present invention provides a breast prosthesis comprising:
a breast prosthesis; and
a drug layer bound onto the breast prosthesis or a part thereof,
wherein the drug layer consists of composites comprising drug-loaded particles and a biocompatible polymer, wherein the drug-loaded particles consist of composites comprising a drug and a biocompatible polymer.

Preferably, the breast prosthesis further comprises a water-soluble polymer layer, which consists of a water-soluble polymer covering the upper portion of the drug layer.

As used herein, the term "breast prosthesis" refers to a medical product for maintaining the shape or size of breasts when performing mastoplasty for the purpose of breast reconstruction or for beauty purposes.

In performing the breast reconstruction operation according to the present invention, the breast prosthesis can be inserted into the body after securing a space via expansion of skin and soft tissues by placing a tissue expander, which is coated with drug delivery particles on its surface, in the body for a predetermined period of time, or the prosthesis can be inserted without inserting the tissue expander. The tissue expander may use saline, but is not limited thereto.

Additionally, the tissue expander, which is coated with drug delivery particles on its surface, can alleviate infections, inflammations, or foreign body reactions via drug delivery while it is inserted into the body.

In the present invention, examples of breast prosthesis may include conventional silicone bag prosthesis, silicone gel prosthesis, or cohesive silicone gel prosthesis, etc., but it is not limited thereto.

As used herein, the term "drug layer" refers to a layer which contains a drug.

The present invention provides a breast prosthesis intending to ensure tropical delivery of a drug by directly binding a drug delivery system to the surface of the breast prosthesis, hence maximizing its therapeutic effects.

Additionally, the drug delivery system of the breast prosthesis can control the duration of drug release using an external energy to control drug release behavior and, based on the same, it can maximize its therapeutic effects such as a pharmaceutical non-invasive contracture plasty Examples of the above external energy may include ultrasonic waves, low frequency waves, heat transfer, mechanical pressure, negative pressure, positive pressure, lasers, LEDs, ionized radiation, low-level laser therapy (LLLT) or electromagnetic fields, but it is not limited thereto. In the case of the ultrasonic waves, those over the entire wavelength region may be used as an energy source. For LEDs, 830 nm may be generally used, but they are not limited thereto.

In the case of a conventional breast prosthesis embodied for practical drug delivery, a drug layer is formed such that the drug component is impregnated into a polymer substance, etc., and thereby its surface is coated therewith. In this case, there are disadvantages in that an adverse reaction may occur due to a rapid drug release at the initial stage and in that there is a difficulty in embodying the long-term drug delivery feature.

In the present invention, drug-loaded particles are formed by first using a biocompatible polymer, and then a drug layer is formed thereafter by binding the drug-loaded particles onto the surface of a breast prosthesis using the biocompatible polymer, thereby enabling controlled delivery of a drug.

That is, the present invention can control the release behavior of a given drug via diffusion of the drug caused by decomposition or disintegration of the polymer that constitutes the particles, or the polymer used for binding the polymer to the particles in the form of a layer. Specifically, the diffusion rate can be controlled by the particle size, the kinds of polymer, the thickness of layer, the number of drug layer or a combination thereof.

As described above, since the diffusion rate of a drug can be controlled by adjusting the number of drug layers and/or the particle size, various drug delivery features may be obtained by applying combinations of various drug layers and particle sizes. Accordingly, the drug layer comprising the drug-loaded particles of the present invention may be a single layer or a multiple layer. Specifically, the number of the drug layers of the present invention may be from one to five, but are not limited thereto.

In an exemplary embodiment, the drug layer may be a combination of two to five layers consisting of equal-sized particles and a biocompatible polymer.

Additionally, in an exemplary embodiment, the drug layer may be a single layer consisting of composites which comprising a combination of various-sized particles and a biocompatible polymer.

Additionally, in an exemplary embodiment, the drug layer may be a single layer or a combination of two to five layers consisting of composites which comprise particles loaded with the same drug and a biocompatible polymer.

In the present invention, the drug may be an antibiotic, a Leukotriene antagonist, a non-steroidal anti-inflammatory agent, or a combination thereof.

Specifically, the drug may be zafirlukast, pranlukast, montelukast, zileuton, gentamycin, vancomycin, penicillin, lincomycin, flurbiprofen, ibuprofen, ketoprofen, or a combination thereof, but is not limited thereto.

Additionally, the drug may be an antifibrotic agent, an antiproliferative agent, an anti-ischemic agent, an anticoagulant, or a combination thereof, but is not limited thereto.

The antifibrotic agent may be pirfenidone, mitomycin, acetylsalicylic acid, genistein, selenocystine or tranilast, but is not limited thereto.

The antiproliferative agent may be tamoxifen, holofuginone, vitamin C, asiaticoside, cyclosporine A, homoharringtonine, vitamin A, D-penicillamine, or liposome, but is not limited thereto.

The anti-ischemic agent may be Necrox-5 or Necrox-7, and the anticoagulant may be a tissue-type plasminogen activator, usokinase (a thrombolytic agent), heparin or suramin, but is not limited thereto.

The particles used in the present invention are not particularly limited regarding their shape, and particles in the form of a sphere, cylinder, film, etc., may be used as necessary.

Preferably, the particles used in the present invention are nanoparticles. As used herein, the term "nano" refers to the size of a particle (diameter or length) on the scale of a few nanometers. Preferably, the size of the nanoparticles of the present invention may be in the range of 1 to 100 nm.

Additionally, the particles used in the present invention are preferably microparticles. As used herein, the term "micro" refers to the size of a particle (diameter or length) on the scale of a few hundred micrometers (μm). Preferably, the size of the microparticles of the present invention may be in the range of 100 to 500 μm.

Additionally, the particles used in the present invention are preferably milliparticles. As used herein, the term "milli" refers to the size of a particle (diameter or length) being on the scale of a few tens to a few hundred millimeters (mm). Preferably, the size of the milliparticles of the present invention may be in the range of 1 to 50 mm.

As used herein, the term "biocompatible polymer" refers to a polymer having biocompatibility and not causing graft rejection after or during an implant surgery in the body. That is, any polymer which has the biocompatibility allowing it to be used in breast prosthesis may be used without limitation, as the polymer for particles or the polymer for forming a drug layer in the present invention. However, the polymer is more preferably a biodegradable polymer that can be biodegraded over time from the aspect of drug release. Preferably, a biodegradable polymer which can be biodegraded in the body over a maximum period of 3 months may be selected and used. When the biodegradable polymer biodegrades in less than the above period, the drug is rapidly released, thus not enabling long-term drug release. In contrast, when the biodegradable polymer is not biodegraded within the above period, it may induce inflammation in the body.

Specifically, examples of the biocompatible polymer with biodegradability may include poly(lactic acid), poly(glycolic acid), poly(lactic-co-glycolic acid), poly(ethylene glycol), poly(trimethylene carbonate), poly(caprolactone), poly(dioxanone), etc., but it is not limited thereto. Additionally, examples of a biocompatible polymer without biodegradability may include poly(methyl methacrylate), polyethylene (PE), polytetrafluoroethylene (PTFE), polyvinyl chloride (PVC), polydimethylsiloxane (PDMS), polyurethane (PU), etc., but it is not limited thereto. The biocompatible polymer may be a biodegradable polymer, a polymer without biodegradability, or a copolymer thereof, and may be a blend in which at least two polymers are mixed therein. That is, the biocompatible polymer may be at least one selected from the group consisting of poly(lactic acid), poly(glycolic acid), poly(lactic-co-glycolic acid), poly(ethylene glycol), poly(trimethylene carbonate), poly(caprolactone), poly(dioxanone), poly(methyl methacrylate), polyethylene(PE), polytetrafluoroethylene (PTFE), polyvinyl chloride (PVC), polydimethylsiloxane (PDMS), polyurethane (PU), and a copolymer thereof, but is not limited thereto.

As used herein, the term "water-soluble polymer layer" refers to a layer comprising a water-soluble polymer. In the present invention, the water-soluble polymer layer is designed to bind onto a breast prosthesis so that it can cover the upper portion of a drug layer bound onto the breast prosthesis, thereby being capable of immobilizing and protecting the drug layer. The water-soluble polymer layer, upon its implantation into a body, is rapidly dissolved and disappears, thereby exposing the drug layer and subsequently initiating the release of the drug into the neighboring tissues.

Preferably, the water-soluble polymer layer of the present invention may be a layer consisting of a water-soluble polymer.

In the present invention, the water-soluble polymer layer may be polyvinyl alcohol (PVA), polyethylene glycol (PEG), polyacrylamide (PAAM), polyvinylpyrrolidone (PVP), hydroxypropylcellulose (HPC), hydroxypropylmethylcellulose (HPMC) or carboxymethyl ethyl cellulose (CMEC), but is not limited thereto.

Additionally, the present invention provides a method for manufacturing a breast prosthesis including:
preparing drug-loaded particles (step 1);
preparing a film consisting of composites, which comprise the particles and a biocompatible polymer (step 2); and
binding the film onto the breast prosthesis (step 3).

Preferably, the method may further comprising binding a water-soluble polymer layer to the film to cover the upper portion thereof (step 4) after step 3.

Step 1 above relates to preparation of drug-loaded particles, i.e., a step of preparing drug-loaded particles for controlled release of a drug.

In the present invention, the drug-loaded particles in step 1 may consist of composites comprising a drug and a biocompatible polymer for the controlled release of the drug as described above.

In the present invention, the drug-loaded particles may be prepared according to a conventional method or purchased from the commercial market.

Specifically, the drug-loaded particles may be prepared by methods such as phase separation, interfacial polymerization, single/double emulsion, spray drying, and fluidized bed.

The type of drugs, size of particles, and kinds of biocompatible polymers are the same as described in the explanation on the breast prosthesis.

Step 2 above relates to preparation of a film consisting of composites comprising the particles and a preparation of drug-loaded particles, i.e., a step of preparing a film by mixing the particles and the biocompatible polymer.

In the present invention, the preparation of the film in step 2 may be performed via solution casting or electrospinning.

Specifically, step 2 above may comprise:
2-1) mixing particles and a biocompatible polymer solution or melt (step 2-1);
2-2) adding the mixture into a mold and preparing it in the form of a film (step 2-2); and
2-3) drying the film (step 2-3).

Step 2-1 above relates to a mixing of the particles and the biocompatible polymer solution or melt, i.e., mixing of the particles and the biocompatible polymer solution or melt and preparing the mixture in the form of a film.

The biocompatible polymer solution can be prepared by dissolving the biocompatible polymer in a solvent. In particular, the kinds of biocompatible polymers to be used are the same as described in the explanation on the breast prosthesis. The solvent may be selected according to the kinds of the biocompatible polymers. Specifically, examples of the usable solvents may include organic solvents such as dimethylformamide (DMF), tetrahydrofuran (THF), and methyl chloroform (MC), but are not limited thereto.

The biocompatible polymer melt can be obtained by melting the biocompatible polymer without an additional solvent.

The mixture obtained by mixing the biocompatible polymer solution or melt with particles may be in the state of a liquid or dough suitable for molding it in the form of a film.

Step 2-2 above relates to preparation of a film by adding the mixture into a mold, i.e., molding the mixture in the form of a film.

The mold may be manufactured using a master mold after manufacturing the master mold in the shape same as that of the film to be formed. The master mold may be manufactured into a desirable shape using a poly(methyl methacrylate) (PMMA) sheet, poly(carbonate) (PC) sheet, poly(ethylene terephthalic acid) (PET) sheet, poly(ethylene naphthalate) (PEN) sheet, etc. In manufacturing molds using the master mold, the usable materials for molding include poly(dimethylsiloxane) (PDMS), but are not limited thereto, and any material conventionally used in the art may be appropriately selected and used.

Additionally, the film may be in various shapes including a circle, a rectangle, a triangle, a polygon, etc., but is not limited thereto.

Step 2-3 above relates to the drying of the film, i.e., drying the film so that it can be hardened.

The usable drying methods are not particularly limited. However, for protection of the characteristics of the materials, lyophilization is preferred, and in particular, for removal of remaining solvent via high vacuum, vacuum lyophilization is preferred. Specifically, the lyophilization is preferably performed at a temperature between $-40°$ C. and $-50°$ C. Meanwhile, the lyophilization may be performed for from 12 hours to 48 hours.

Step 3 above relates to binding of the film onto the breast prosthesis, i.e., binding the film comprising the drug-loaded particles onto the breast prosthesis by distinguishing the dome and the base of the breast prosthesis to enable a controlled release of the drug.

In the present invention, the film binding in step 3 may be performed so that the film can cover the entire breast prosthesis, and additionally, it may be further performed by a method using patterns such as a lattice, a point, a letter, or a non-letter by random coating, but is not limited thereto.

Step 4 relates to binding a water-soluble polymer layer to the film to cover the upper portion thereof, i.e., binding the water-soluble polymer layer to immobilize or protect the film comprising the drug.

The types of water-soluble polymers usable in the water-soluble polymer layer are the same as described in the explanation on the breast prosthesis.

Additionally, the present invention provides a method for manufacturing a breast prosthesis comprising:
preparing drug-loaded particles (step 1);
preparing a mixture by mixing the particles and a biocompatible polymer (step 2); and
binding the mixture onto the breast prosthesis in the form of a layer (step 3).

Preferably, the method may further comprise binding a water-soluble polymer layer to the drug-containing layer to cover the upper portion thereof (step 4) after step 3.

Preferably, the method may further comprise drying the breast prosthesis onto which the layer is bound (step 5) after step 3 or step 4.

Step 1 above relates to preparation of drug-loaded particles, and is the same as described in the explanation of the method of manufacturing the breast prosthesis.

Step 2 above relates to preparation of a mixture by mixing the particles and a biocompatible polymer, i.e., preparing a mixture between particles and a biocompatible polymer for forming a layer.

The particles may be in the form of powder suitable to be bound in the form of a layer.

The biocompatible polymer may be mixed in the form of powder, in the form of a solution by dissolving it in a solvent, or may be mixed in the form of a melt without an additional solvent. That is, the mixture between the particles and the biocompatible polymer may be in the form of dough, powder, or a liquid suitable for binding in the form of a layer.

In particular, the kinds of the usable biocompatible polymers are the same as described in the explanation on the breast prosthesis. Additionally, the solvent may be appropriately selected according to the kinds of the biocompatible polymers, specifically, an organic solvent such as dimethylformamide (DMF), tetrahydrofuran (THF), and methyl chloroform (MC) may be used, but is not limited thereto.

Step 3 relates to binding the mixture onto the breast prosthesis in the form of a layer, i.e., directly binding the mixture containing the drug-loaded particles onto the breast prosthesis for the controlled release of the drug.

In the present invention, the binding in step 3 may be performed via spraying, dip coating, electrospinning, dropping or brushing, but is not limited thereto.

In the present invention, a breast prosthesis with a multilayered structure comprising from 2 to 5 drug layers may be manufactured by performing step 3 repeatedly from 2 to 5 times.

Step 4 relates to binding a water-soluble polymer layer to cover the upper portion of the drug-containing layer, i.e., binding a water-soluble polymer layer to cover the upper portion of the drug-containing layer for the purpose of immobilizing or protecting the drug-containing layer.

The kinds of the water-soluble polymers usable in the water-soluble polymer layer are the same as described in the explanation on the breast prosthesis.

Step 5 above relates to drying a breast prosthesis onto which the above layer is bound, i.e., drying a breast prosthesis onto which a mixture comprising the drug-loaded particles or a water-soluble polymer is bound in the form of a layer.

The usable drying methods are not particularly limited. However, for protection of the characteristics of the materials, lyophilization is preferred, and in particular, for removal of remaining solvent via high vacuum, vacuum lyophilization is preferred. Specifically, the lyophilization is preferably performed at a temperature between −40° C. and −50° C. Meanwhile, the lyophilization may be performed for 12 hours to 48 hours.

The constitutional features of the present invention are explained in detail with reference to the accompanying drawings below.

The present invention can provide a breast prosthesis capable of controlling the release behavior of a given drug via diffusion of the drug through a particle-constituting polymer or a drug layer-constituting polymer or via the decomposition rate of the polymer, by forming a drug layer on the breast prosthesis using biocompatible polymers and particles, followed by the preparation of the particles to be loaded with a drug.

Advantageous Effects

The present invention is advantageous in that it can provide a breast prosthesis allowing controlled release of a drug by binding a drug layer comprising drug-loaded particles onto the breast prosthesis.

MODE FOR INVENTION

A better understanding of the present invention regarding its constitutional features and effects may be obtained through the following examples which are set forth to illustrate, but are disclosed for illustrative purposes only and are not to be construed as limiting the present invention.

EXAMPLE

Preparation of Drug-Loaded Particles

A breast prosthesis according to the present invention was manufactured as described below, in particular, the breast prosthesis was manufactured so that the drug-loaded milliparticles could be coated onto an implant.

Figure 1:
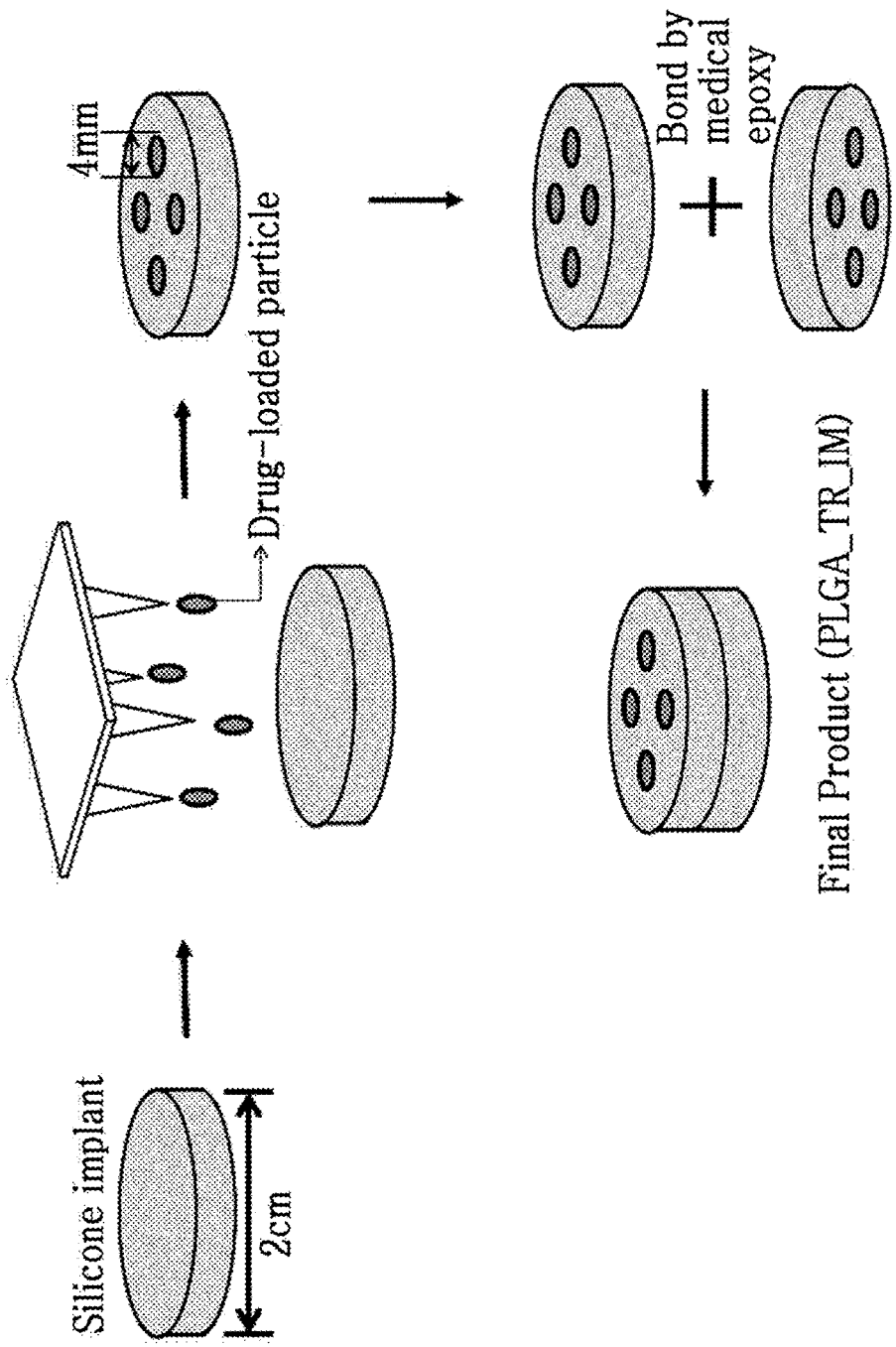
FIG. 1 is a schematic diagram illustrating the process of manufacturing a silicone implant, the surface of which is coated with drug-loaded milliparticles according to an example of the present invention.

Tranilast, an antifibrotic agent, was mixed with poly (lactic-co-glycolic acid) (PLGA, drug delivery system) (10% w/w), dissolved in DMF, an organic solvent, and then 10 μL each of the resultant was dropped on the surface of a flat silicone implant to thereby coat the drug-loaded milliparticles thereon. In particular, a total of four milliparticles were formed, and each milliparticle had a diameter of 4 mm. As such, two silicone implants, whose surfaces were coated with the drug-loaded milliparticles, were manufactured, and the inner surfaces (the opposite surfaces), which were not coated with the drug-loaded milliparticles, were joined with medical epoxy to face with each other, thereby manufacturing silicone implants coated with the milliparticles, loaded with the drugs for efficacy evaluation (PLGA_TR_IM). The process of manufacturing the silicone implant coated with the drug-loaded milliparticles (PLGA_TR_IM) is shown in FIG. 1.

Comparative Example 1

Preparation of Untreated Implants

An untreated implant (IM) prepared by joining two silicone implants with epoxy was manufactured, and was used as a control group for evaluation of drug efficacies.

Comparative Example 2

Preparation of implants treated with PLGA

Poly(lactic-co-glycolic acid) (PLGA, drug delivery system) (10% w/w) was dissolved in DMF, an organic solvent, and then 10 μL each of the resultant was dropped on the surface of a flat silicone implant to thereby coat the PLGA surface. As such, two silicone implants, whose surfaces were coated with the PLGA, were manufactured, and the inner surfaces (the opposite surfaces), which were not coated with PLGA, were joined with medical epoxy to face with each other, thereby manufacturing silicone implants coated with only PLGA (PLGA_IM). The resulting implant was used as a control group for evaluation of drug efficacies.

Experimental Example 1

In Vitro Analysis of Drug Release

A drug release experiment regarding the release of tranilast, an antifibrotic agent, was performed using the silicone implant (PLGA_TR_IM) coated with the drug-loaded milliparticles prepared in Example. Before the release experiment, the amount of the drug loaded in each drop (10 μL) was measured and shown in Table 1 below.

As shown in Table 1 below, it was confirmed that the amount of the drug loaded in each drop was similar to that of the theoretical value.

TABLE 1

| Category | Amount of drug loaded (μg/10 μL (per drop)) |
|---|---|
| Theoretical value | 20 |
| Experimental value | 18.4 ± 0.19 |

Based on the above result, a drug release experiment was performed using the silicone implant (PLGA_TR_IM), whose surface was coated with the drug-loaded milliparticles prepared in Example. After putting the silicone implant sample (n=5) whose surface was coated with the drug-loaded milliparticles prepared in Example (PLGA_TR_IM) into 5 mL of PBS (pH 7.4, 37° C.), 2 mL each of a liquid of release was collected therefrom at predetermined dates (day 1, 3, 5, 7, 10 and 14), respectively. The respective amount of the drug release contained in each of the liquid of release collected at the predetermined dates was measured, and an equal volume (2 mL) of PBS (pH 7.4, 37° C.) was added thereinto to replenish the loss, and the result of the drug release experiment is shown in FIG. 2.

Figure 2:
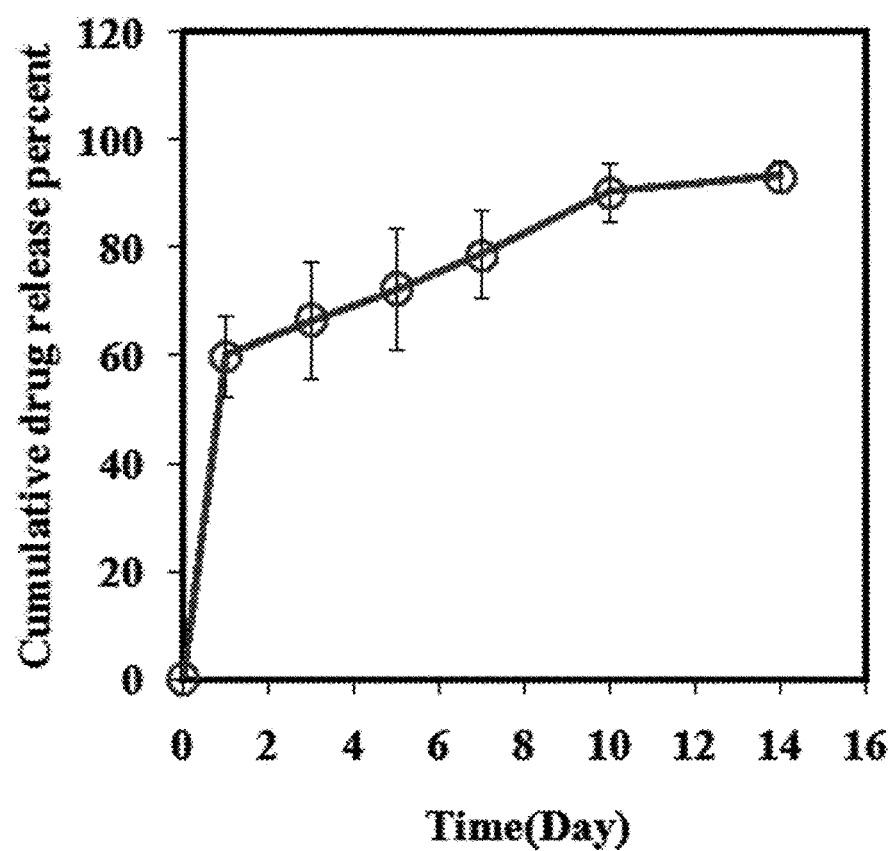
FIG. 2 is a graph illustrating the experimental result on the release of a drug loaded on milliparticles according to an example of the present invention.

As shown in FIG. 2, the initial burst of the drug on day 1 was about 60%, and the remaining 40% was slowly released over the following 13 days. Accordingly, it was confirmed that the drug was released continuously over a 14 day period (two weeks).

Additionally, as shown in FIG. 2, the breast prosthesis coated with the milliparticles prepared above can be coated further with a biocompatible polymer to induce a release pattern of a desired drug.

Experimental Example 2

In-Vivo Analysis of Antifibrotic Effect

The antifibrotic effect of the drug was analyzed using an experimental animal model based on the result of Experimental Example 1. An eight-week old rat (250 g-300 g) was implanted with three kinds of samples (IM, PLGA_IM and PLGA_TR_IM) prepared in Example and Comparative Example 1-2 underneath the skin on its back region. In particular, IM represents a sample without any treatment, PLGA_IM represents a silicone implant sample coated with only a biodegradable polymer (PLGA), i.e., a drug delivery system, and PLGA_TR_IM represents a sample, whose surface was coated with drug-loaded milliparticles prepared in Example. Each sample was implanted into to five rats on their back, and a histological evaluation was performed via H&E Staining to confirm the thickness of their fibrous capsules for the evaluation of drug efficacies.

On the second week of the implantation, the rats implanted with each of the samples were sacrificed, the tissues adjacent to the samples were biopsied and the degree of fibrous capsule formation was observed under a microscope via H&E Staining and their images were obtained therefrom. Based on the images, the thickness of fibrous capsules was measured from the above region of muscle and the results are shown in Table 2 below and FIG. 3.

TABLE 2

| Category | IM | PLGA_IM | PLGA_TR_IM |
|---|---|---|---|
| thickness of fibrous capsule (μm) | 1082.32 ± 90.25 | 1092.39 ± 63.02 | 874.58 ± 67.07 |

Figure 3:
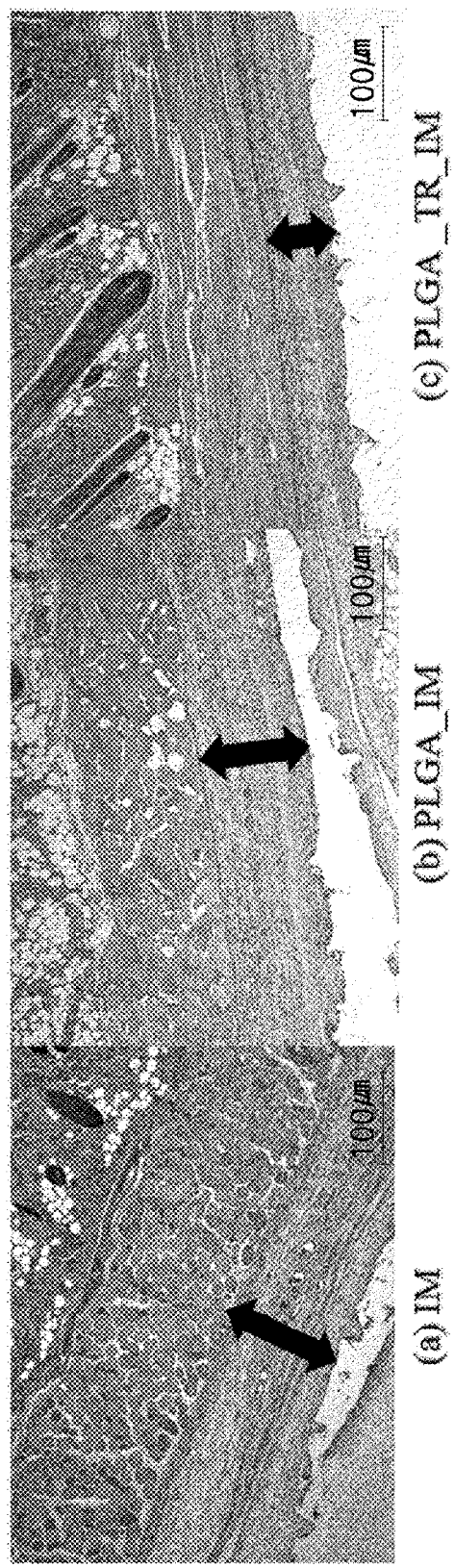
FIG. 3 shows microscopic images of the changes in the thickness of fibrous capsules after implantation of each sample, wherein (a) represents an intact implant (IM), (b) PLGA_IM (an implant coated with only PLGA) and (c) PLGA_TR_IM (an implant coated with a mixture of PLGA and tranilast (a drug)), according to an example of the present invention.

As shown in Table 2 above and FIG. 3, the thickness of the fibrous capsule with IM implantation was 1082.32±90.25 µm, that with PLGA_IM implantation was 1092.39±63.02 µm, and that with IM was similar to that of the experimental group. Meanwhile, the thickness of the fibrous capsule in the rats implanted with PLGA_TR_IM was 874.58±67.07 µm, which was thinner than those in the experimental groups implanted with IM and PLGA_IM. Accordingly, it was confirmed that the silicone implant whose surface was coated with the particles loaded with the drug of the present invention (PLGA_TR_IM) had an antifibrotic effect, and this indicates that the antifibrotic effect is due to the drug released from the drug-loaded particles.

Figure 4:
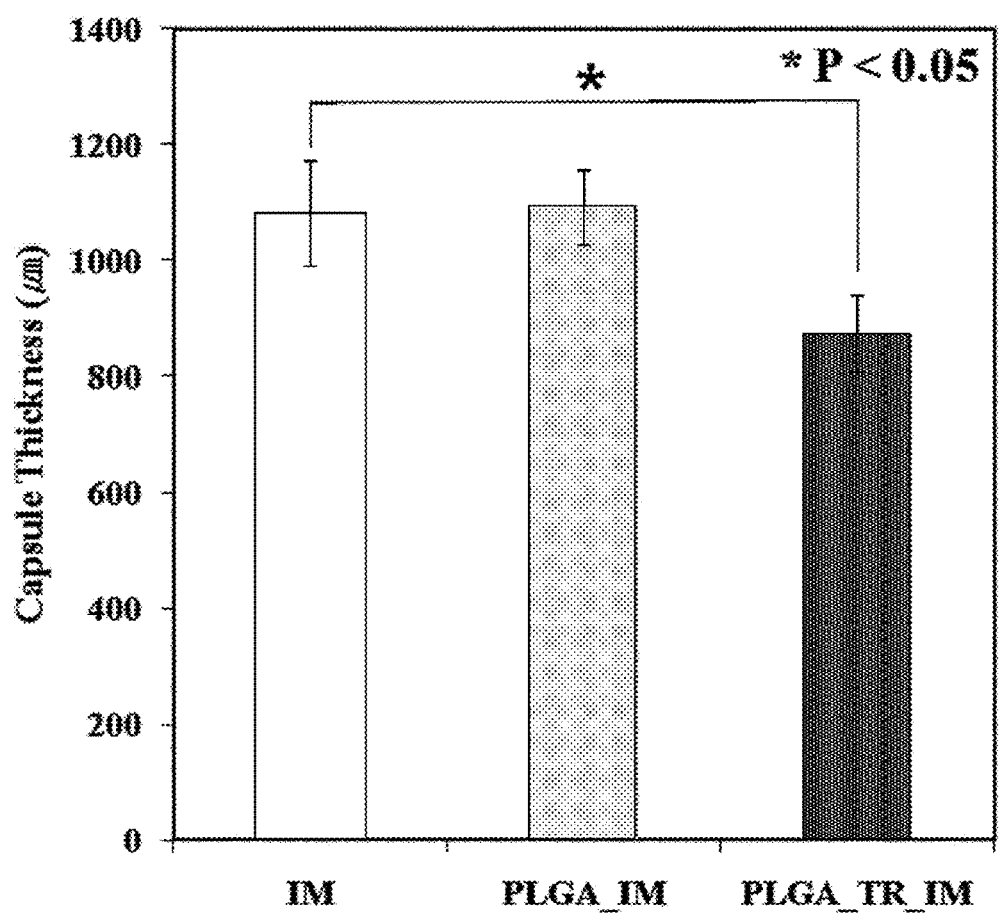
FIG. 4 is a graph illustrating the analysis result of statistical significance among each group regarding the changes in the thickness of fibrous capsules after implantation of each sample, wherein (a) represents an intact implant (IM), (b) PLGA_IM (an implant coated with only PLGA) and (c) PLGA_TR_IM (an implant coated with a mixture of PLGA and tranilast (a drug)), according to an example of the present invention.

Additionally, a statistical analysis was performed via Anova one-way (SPSS program) in order to confirm the significance of the analysis of the antifibrotic effect due to the implantation of each sample, and the results are shown in FIG. 4.

As shown in FIG. 4, the result of statistical analysis between IM and PLGA_TR_IM was shown to be of significance ($p<0.05$). Accordingly, the silicone implant whose surface was coated with the milliparticles loaded with a drug prepared in Example of the present invention (PLGA_TR_IM) had a significant drug release effect from the statistical point of view.

A breast prosthesis capable of controlled release of a drug according to an exemplary embodiment of the present invention will be explained in detail below with reference to the accompanying drawings.

Figure 5:
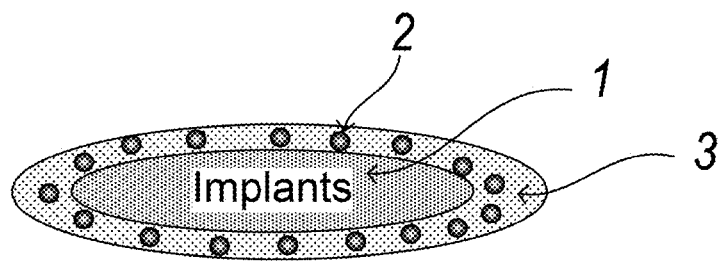
FIG. 5 is a schematic diagram illustrating a structure of a breast prosthesis having a single drug layer, according to an exemplary embodiment of the present invention.

FIG. 5 is a schematic diagram illustrating a structure of a breast prosthesis having a single drug layer, according to an exemplary embodiment of the present invention.

In FIG. 5, the breast prosthesis of the present invention includes a breast prosthesis (1); and a drug layer bound onto the breast prosthesis (1) consisting of composites, which comprise drug-loaded particles (2) and a biocompatible polymer (3).

Figure 6:
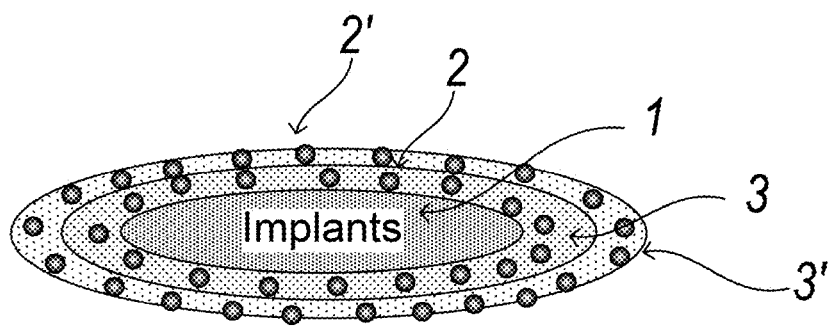
FIG. 6 is a schematic diagram illustrating a structure of a breast prosthesis, which has two drug layers consisting of composites comprising drug-loaded particles and a biocompatible polymer, according to an exemplary embodiment of the present invention.

FIG. 6 is a schematic diagram illustrating a structure of a breast prosthesis, which has two drug layers consisting of composites comprising drug-loaded particles and a biocompatible polymer, according to an exemplary embodiment of the present invention.

In FIG. 6, the breast prosthesis of the present invention includes a breast prosthesis (1); and two drug layers bound onto the breast prosthesis (1) consisting of composites, which comprise different drug-loaded particles (2, 2') and biocompatible polymers (3, 3'), respectively.

Figure 7:
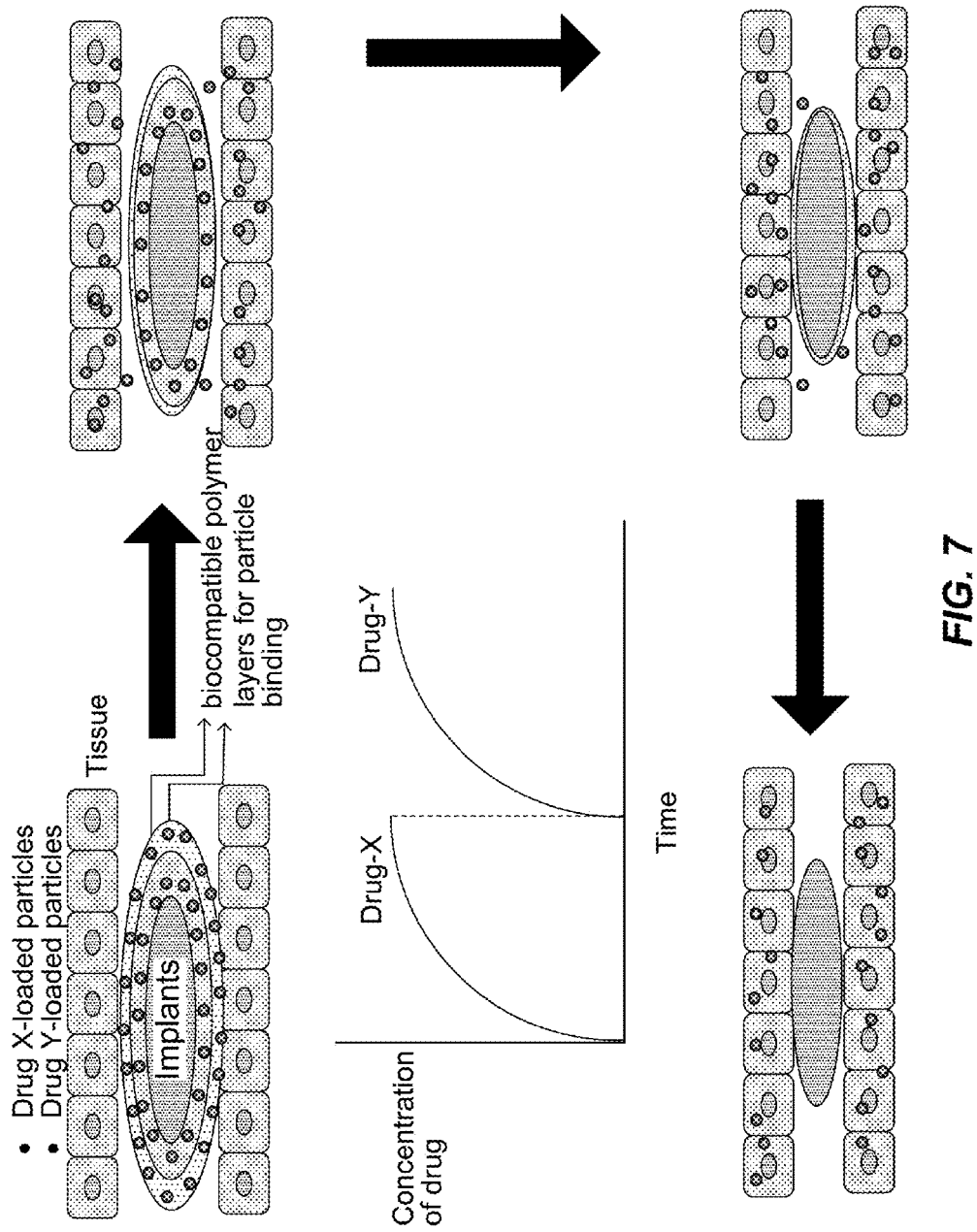
FIG. 7 is a schematic diagram illustrating a method of drug release into neighboring tissues in a breast prosthesis, which has the above two drug layers after implantation, according to an exemplary embodiment of the present invention.

FIG. 7 is a schematic diagram illustrating a method of drug release into neighboring tissues in a breast prosthesis, which has the above two drug layers after implantation, according to an exemplary embodiment of the present invention.

As shown in FIG. 7, the drug may be released in such a manner that an externally located drug layer of the two drug layers, which include the mutually different drug-loaded particles, is decomposed or disintegrated first and releases a drug for a certain period of time, followed by a release of a drug from an internally located drug layer.

Figure 8:
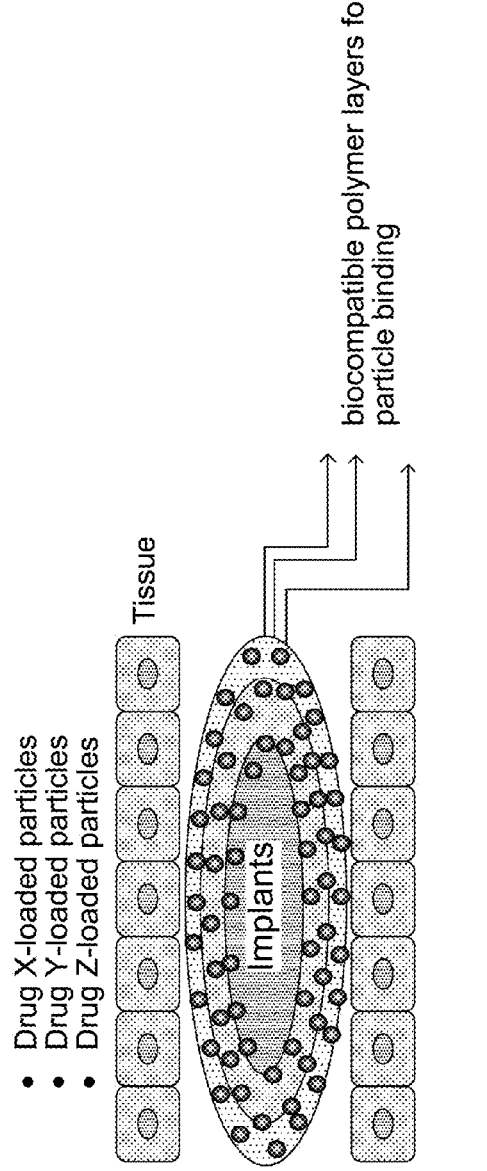
FIG. 8 is a schematic diagram illustrating a method of drug release into neighboring tissues in a breast prosthesis, which has three drug layers consisting of composites comprising particles loaded with different drugs and a biocompatible polymer after implantation, according to an exemplary embodiment of the present invention.
Figure 8:
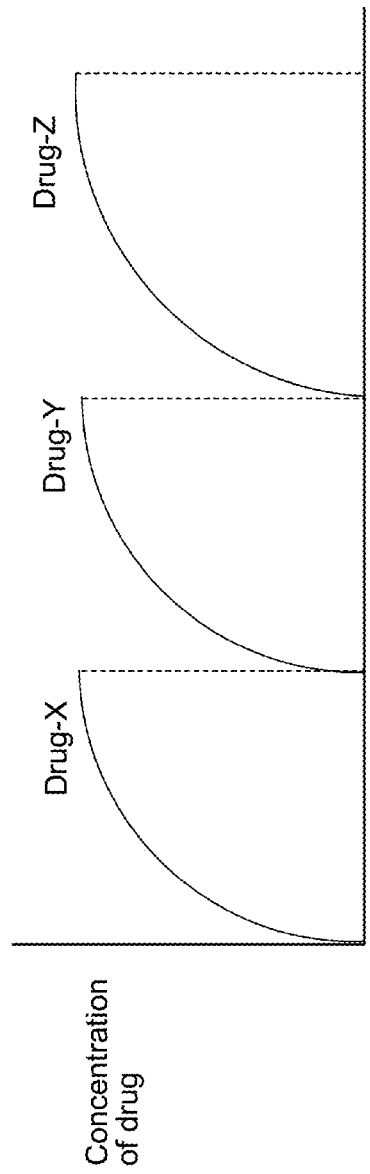

FIG. 8 is a schematic diagram illustrating a method of drug release into neighboring tissues in a breast prosthesis, which has three drug layers consisting of composites comprising particles loaded with different drugs and a biocompatible polymer after implantation, according to an exemplary embodiment of the present invention.

As shown in FIG. 8, the drug may be released in such a manner that a most externally located drug layer among the three drug layers, which comprise the mutually different drug-loaded particles, is decomposed or disintegrated first and releases a drug for a certain period of time, a drug layer located at an intermediate position releases a drug for a certain period of time, and finally an internally located drug layer releases a drug.

Figure 9:
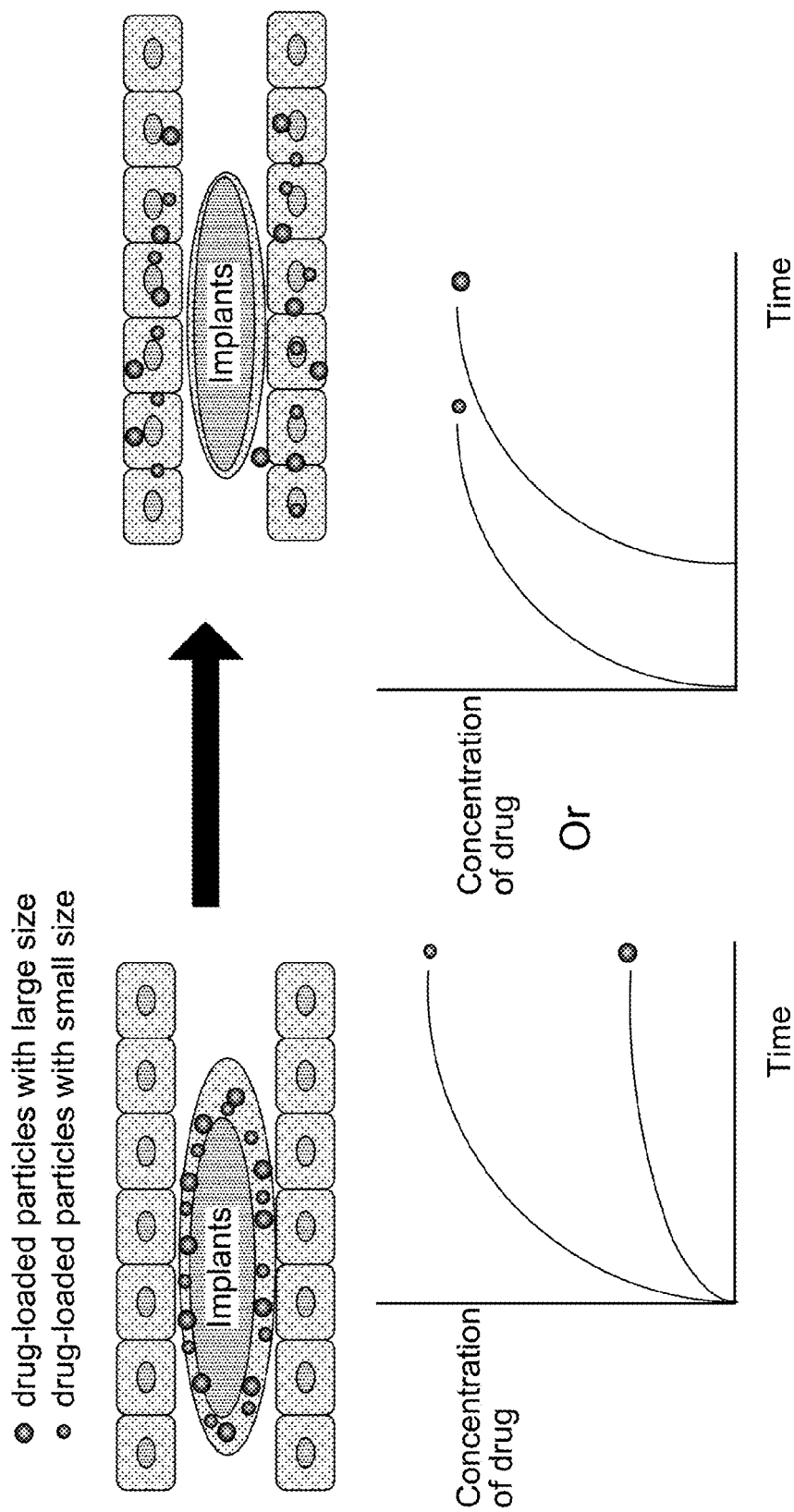
FIG. 9 is a schematic diagram illustrating a method of drug release into neighboring tissues in a breast prosthesis, which has a single drug layer consisting of composites comprising particles loaded with the same drug but of various-sized particles and a biocompatible polymer after implantation, according to an exemplary embodiment of the present invention.

FIG. 9 is a schematic diagram illustrating a method of drug release into neighboring tissues in a breast prosthesis, which has a single drug layer consisting of composites comprising particles loaded with the same drug but of various-sized particles and a biocompatible polymer after implantation, according to an exemplary embodiment of the present invention.

As shown in FIG. 9, although small-sized particles and large-sized particles are simultaneously released into the neighboring tissues by the decomposition or disintegration of the biocompatible polymer that constitutes the drug layer, the drug may be released in such a manner that the smaller-sized particles of the above particles are more easily decomposed or disintegrated and release a drug first, and then larger-sized particles release a drug thereafter.

A more versatile controlled release of a drug may be possible when the methods of controlled release of drugs according to the number of drug layers as shown in FIG. 7 or FIG. 8, and the method of controlled release of drugs according to particle size shown in FIG. 9 are combined.

Figure 10:
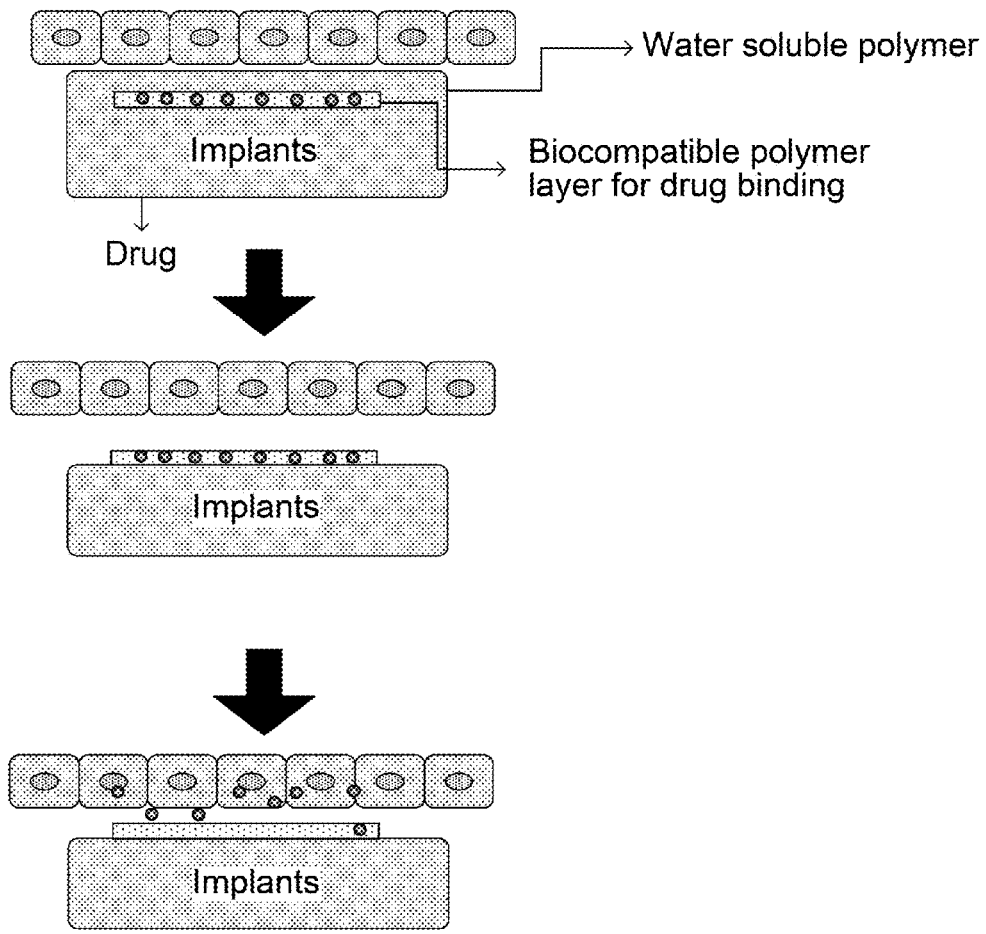
FIG. 10 is a schematic diagram illustrating a method of drug release into neighboring tissues in a breast prosthesis, wherein a drug layer consisting of composites comprising drug-loaded particles and a biocompatible polymer is bound onto part of the breast prosthesis, and the water-soluble polymer layer, which contains water-soluble polymers covering the upper portion of the drug layer, is additionally bound thereonto, after implantation, according to an exemplary embodiment of the present invention.

FIG. 10 is a schematic diagram illustrating a method of drug release into neighboring tissues in a breast prosthesis, wherein a drug layer consisting of composites comprising drug-loaded particles on the scale of nano-, micro-, milli-, or centi-meter, and a biocompatible polymer is bound onto part of the breast prosthesis, and the water-soluble polymer layer, which contains water-soluble polymers covering the upper portion of the drug layer, is additionally bound thereonto, after implantation, according to an exemplary embodiment of the present invention.

As shown in FIG. 10, a drug release may be performed in such a manner that, after the implantation of a breast prosthesis, the water-soluble polymer layer is dissolved and disappears thereby exposing the drug layer, and subsequently the biocompatible polymer constituting the drug layer is decomposed or disintegrated thereby releasing the drug-loaded particles from the drug layer into the neighboring tissue.

In the breast prosthesis of the present invention, when the drug is comprised in the drug layer as it is along with the method of loading it into particles, it can control the drug delivery in the drug layer while the drug delivery is controlled in the particles as well, thereby enabling a more versatile drug release method. In particular, when the kind of the drug being loaded into particles differs from that of the drug being included in the drug layer as it is, a more versatile method of drug release may be possible.

The breast prosthesis of the present invention may be manufactured by binding the breast prosthesis of the present invention directly or indirectly onto the breast prosthesis.

Figure 11:
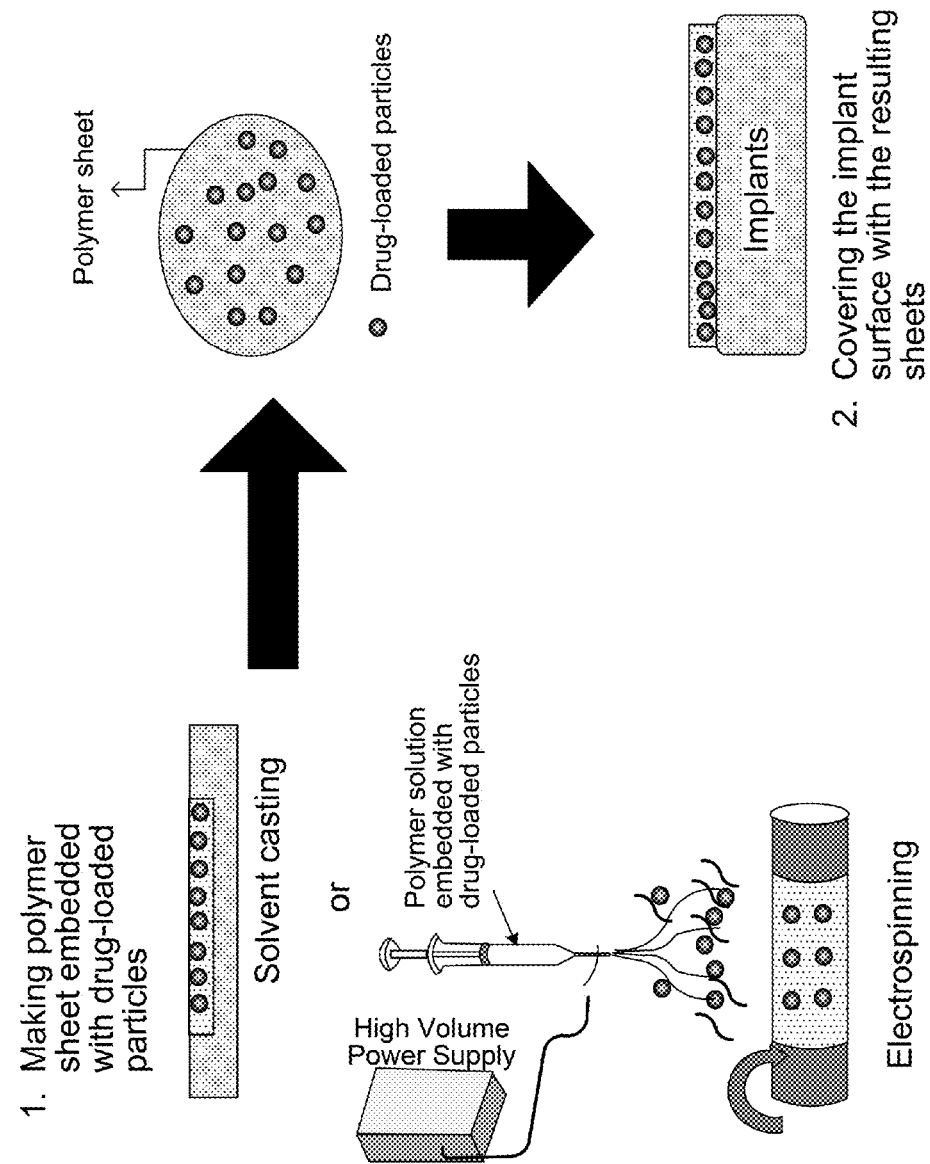
FIG. 11 is a schematic diagram illustrating a method of indirectly binding drug-loaded particles onto a breast prosthesis, wherein a drug layer comprising drug-loaded particles is prepared first in the form of a film, and then bound onto the breast prosthesis, according to an exemplary embodiment of the present invention.

FIG. 11 is a schematic diagram illustrating a method of indirectly binding drug-loaded particles onto a breast prosthesis, wherein a drug layer comprising drug-loaded particles is prepared first in the form of a film, and then bound onto the breast prosthesis, according to an exemplary embodiment of the present invention.

As shown in FIG. 11, a breast prosthesis capable of the controlled release of a drug according to the present invention may be manufactured by first preparing a film via solution casting (solvent casting) or electrospinning followed by covering the surface of the breast prosthesis with the film.

Figure 12:
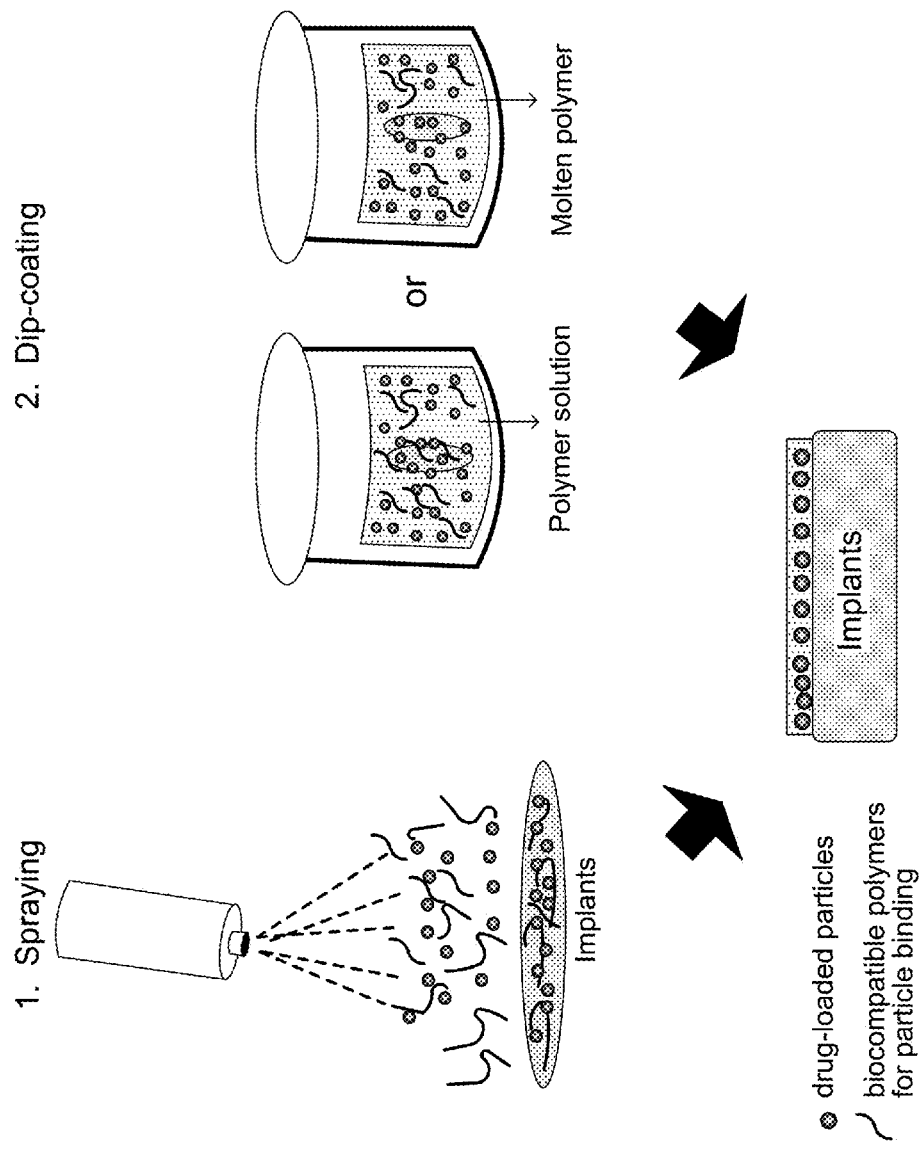
FIG. 12 is a schematic diagram illustrating a method of directly binding drug-loaded particles onto a breast prosthesis, wherein a mixture comprising drug-loaded particles is prepared and then directly bound onto the breast prosthesis via spraying or dip coating, according to an exemplary embodiment of the present invention.

FIG. 12 is a schematic diagram illustrating a method of directly binding drug-loaded particles onto a breast prosthesis, wherein a mixture comprising drug-loaded particles is prepared and then directly bound onto the breast prosthesis via spraying or dip coating, according to an exemplary embodiment of the present invention.

As shown in FIG. 12, a breast prosthesis capable of the controlled release of a drug according to the present invention may be manufactured by first preparing a mixture comprising the drug-loaded particles and a biocompatible polymer followed by directly forming a layer on the surface of the breast prosthesis via spraying or dip coating.

Figure 13:
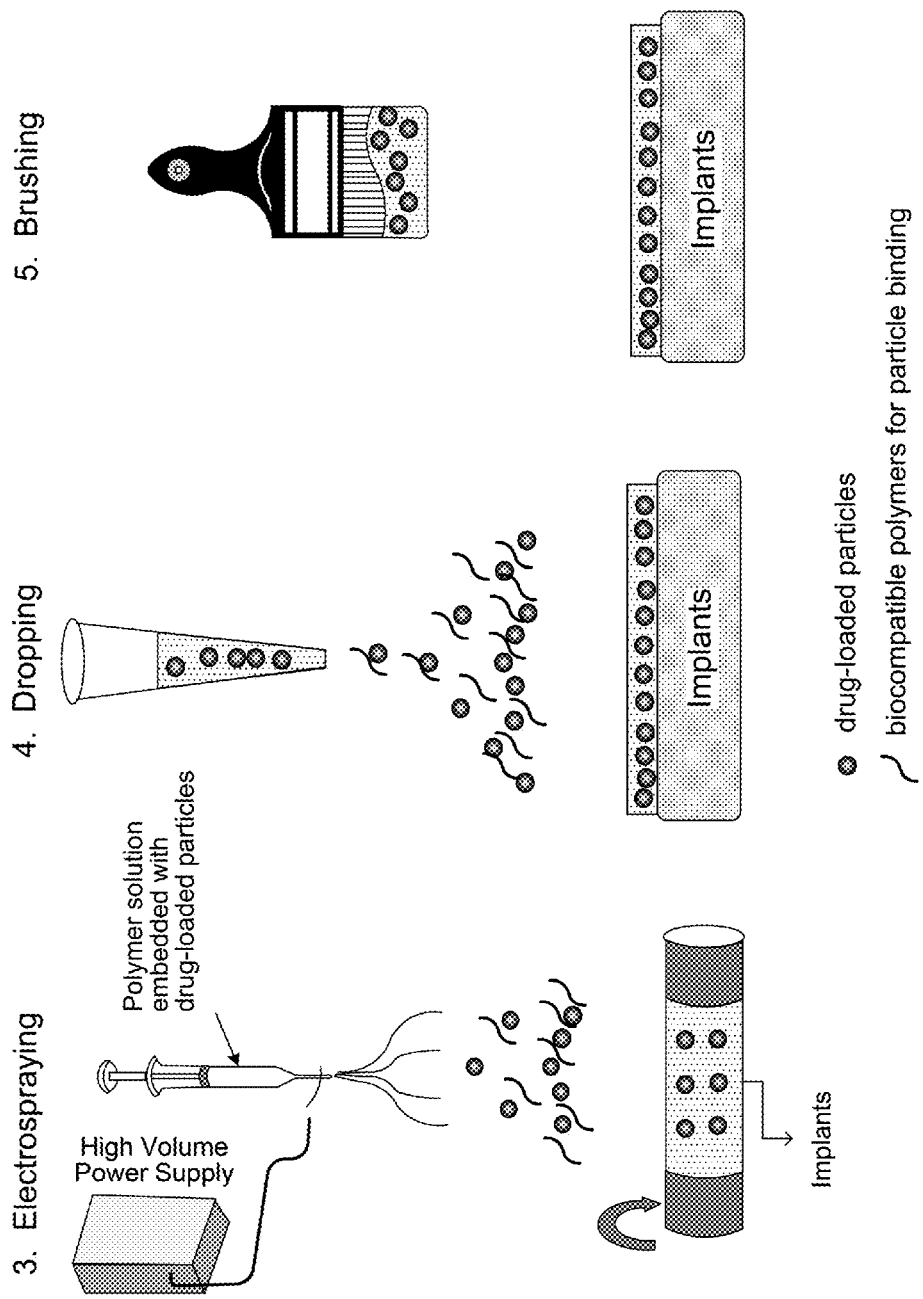
FIG. 13 is a schematic diagram illustrating a method of directly binding drug-loaded particles onto a breast prosthesis, wherein a mixture comprising drug-loaded particles is prepared and then directly bound onto the breast prosthesis via electrospraying, dropping or brushing, according to an exemplary embodiment of the present invention.

FIG. 13 is a schematic diagram illustrating a method of directly binding drug-loaded particles onto a breast prosthesis, wherein a mixture comprising drug-loaded particles is prepared and then directly bound onto the breast prosthesis via electrospraying, dropping or brushing, according to an exemplary embodiment of the present invention.

As shown in FIG. 13, a breast prosthesis capable of the controlled release of a drug according to the present invention may be manufactured by first preparing a mixture comprising the drug-loaded particles and a biocompatible followed by directly forming a layer on the surface of the breast prosthesis via electrospraying, dropping, or brushing using the mixture.

The invention claimed is:

1. A breast prosthesis comprising:
a breast prosthesis,
a drug layer bound onto the breast prosthesis or a part thereof, and
a water-soluble polymer layer covering the upper portion of the drug layer,
wherein the drug layer consists of composites comprising drug-loaded particles and a biocompatible polymer, and
wherein the water-soluble polymer is polyacrylamide (PAAM), hydroxypropylcellulose (HPC) or carboxymethyl ethyl cellulose (CMEC).

2. The breast prosthesis of claim 1, wherein the drug-loaded particles consist of composites comprising a drug and a biocompatible polymer.

3. The breast prosthesis of claim 1, wherein the drug layer is a combination of from 2 to 5 layers consisting of composites comprising equal-sized particles and a biocompatible polymer.

4. The breast prosthesis of claim 1, wherein the drug layer is a single layer consisting of composites, wherein the composite comprises a combination of various-sized particles and a biocompatible polymer.

5. The breast prosthesis of claim 1, wherein the drug is an antibiotic, a Leukotriene antagonist, a non-steroidal anti-inflammatory drug, or a combination thereof.

6. The breast prosthesis of claim 5, wherein the drug is zafirlukast, pranlukast, montelukast, zileuton, gentamycin, vancomycin, penicillin, lincomycin, flurbiprofen, ibuprofen, ketoprofen, meloxicam, piroxicam, ketorolac, or a combination thereof.

7. The breast prosthesis of claim 5, wherein the drug further comprises an adjuvant, wherein the adjuvant is an antifibrotic agent, an antiproliferative agent, an anti-ischemic agent, an anticoagulant or a combination thereof.

8. The breast prosthesis of claim 7, wherein the antifibrotic agent is pirfenidone, mitomycin, acetylsalicylic acid, genistein, selenocystine or tranilast.

9. The breast prosthesis of claim 7, wherein the antiproliferative agent is tamoxifen, holofuginone, vitamin C, asiaticoside, cyclosporine A, homoharringtonine, vitamin A, D-penicillamine or liposome.

10. The breast prosthesis of claim 7, wherein the anticoagulant is a tissue-type plasminogen activator, a usokinase (thrombolytic agent), heparin or suramin.

11. The breast prosthesis of claim 1, wherein the biocompatible polymer is at least one selected from the group consisting of poly(lactic acid), poly(glycolic acid), poly(lactic-co-glycolic acid), poly(ethylene glycol), poly(trimethylene carbonate), poly(caprolactone), poly(dioxanone), poly(methyl methacrylate), polyethylene, polytetrafluoroethylene, polyvinyl chloride, polydimethylsiloxane, polyurethane and a copolymer thereof.

12. A method for manufacturing the breast prosthesis of claim 1, comprising:
preparing drug-loaded particles (step 1);
preparing a film consisting of composites, which comprise the particles and a biocompatible polymer (step 2);
binding the film onto the breast prosthesis (step 3); and
binding a water-soluble polymer layer to the film to cover the upper portion thereof (step 4).

13. The method of claim 12, wherein the manufacturing the film in step 2 is performed via solution casting or electrospinning.

14. A method for manufacturing the breast prosthesis of claim 1, comprising:
preparing drug-loaded particles (step 1);
preparing a mixture by mixing the particles and a biocompatible polymer (step 2);
binding the mixture onto the breast prosthesis in the form of a layer (step 3); and
binding a water-soluble polymer layer to the drug-containing layer to cover the upper portion thereof (step 4).

15. The method of claim 14, further comprising drying the breast prosthesis on which the layer is bound (step 5) after step 4.

16. The method of claim 14, wherein the binding of the layer in step 3 is performed via spraying, dip coating, electrospinning, dropping or brushing.

* * * * *